(12) United States Patent
Kimura et al.

(10) Patent No.: US 8,882,501 B2
(45) Date of Patent: Nov. 11, 2014

(54) DENTAL HANDPIECE WITH SWITCHING VALVE FOR FLUID LINES

(71) Applicants: Takao Kimura, Kanuma (JP); Masanori Mizunuma, Kanuma (JP); Keita Yokochi, Kanuma (JP)

(72) Inventors: Takao Kimura, Kanuma (JP); Masanori Mizunuma, Kanuma (JP); Keita Yokochi, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

(21) Appl. No.: 13/898,371

(22) Filed: May 20, 2013

(65) Prior Publication Data

US 2013/0337402 A1    Dec. 19, 2013

Related U.S. Application Data

(63) Continuation of application No. 13/479,455, filed on May 24, 2012, now abandoned.

(30) Foreign Application Priority Data

May 26, 2011   (JP) ................................. 2011-117768

(51) Int. Cl.
    *A61C 17/00*      (2006.01)
    *A61C 17/02*      (2006.01)
    *A61C 1/00*      (2006.01)

(52) U.S. Cl.
    CPC ......... *A61C 17/0217* (2013.01); *A61C 17/0202* (2013.01); *A61C 1/0061* (2013.01)
    USPC ........................................................ 433/80

(58) Field of Classification Search
    USPC ............ 433/25–166; 137/15.06, 832; 285/34, 285/98, 120.1–121.7, 147.1, 147.15, 190, 285/272–282
    See application file for complete search history.

(56) References Cited

U.S. PATENT DOCUMENTS

| | | | |
|---|---|---|---|
| 2,319,347 A * | 5/1943 | Reed | 137/625.24 |
| 2,576,300 A | 11/1951 | Kreiner | |
| 2,693,373 A | 11/1954 | Tremolada | |
| 4,007,529 A * | 2/1977 | Fleer | 433/104 |
| 4,182,038 A | 1/1980 | Fleer | |
| 4,184,256 A * | 1/1980 | Loge et al. | 433/82 |
| 4,212,640 A * | 7/1980 | Loge et al. | 433/82 |
| 4,213,243 A | 7/1980 | Flatland | |
| 4,217,101 A | 8/1980 | Loge | |
| 4,219,618 A * | 8/1980 | Leonard | 433/80 |
| 4,311,169 A | 1/1982 | Gaillard | |

(Continued)

FOREIGN PATENT DOCUMENTS

| JP | H03 103624 U | 10/1991 |
|---|---|---|
| JP | U-3103624 B | 8/2004 |
| JP | 2010 051343 A | 3/2010 |

*Primary Examiner* — Heidi M Eide
*Assistant Examiner* — Matthew Saunders
(74) *Attorney, Agent, or Firm* — Jason D. Voight

(57) ABSTRACT

A dental handpiece where the chip air line is selectively switched to the ON-state for using both water and chip air, and to the OFF-state for using only water. The dental handpiece has a switching valve between the circumferential chip air channel and the chip air line in the handpiece body for selectively allowing and preventing communication. Opening the valve switches the communication to the ON-state in which chip air is allowed to pass from the circumferential chip air channel into the chip air line. Closing the valve switches the communication to an OFF-state in which chip air is prevented from passing from the circumferential chip air channel into the chip air line.

5 Claims, 7 Drawing Sheets

(56) References Cited

U.S. PATENT DOCUMENTS

| | | | |
|---|---|---|---|
| 4,321,039 A | 3/1982 | Schuss et al. | |
| 4,398,885 A | 8/1983 | Loge et al. | |
| 4,504,227 A | 3/1985 | Lohn | |
| 4,669,982 A | 6/1987 | Fleer | |
| 4,681,540 A * | 7/1987 | Landgraf et al. | 433/126 |
| 5,057,015 A | 10/1991 | Fleer | |
| 5,207,575 A | 5/1993 | Jacoulet et al. | |
| 5,332,194 A | 7/1994 | Austin, Jr. et al. | |
| 5,474,449 A * | 12/1995 | Loge et al. | 433/29 |
| 5,549,634 A | 8/1996 | Scott et al. | |
| 5,846,078 A | 12/1998 | Rosenstatter | |
| 6,305,934 B1 | 10/2001 | Hatley, Jr. | |
| 6,319,003 B2 | 11/2001 | Mosimann | |
| 6,797,332 B2 * | 9/2004 | Strangman et al. | 427/454 |
| 6,826,998 B2 | 12/2004 | Pinot | |
| 6,929,099 B2 | 8/2005 | Jakob et al. | |
| 6,979,322 B2 | 12/2005 | Chu et al. | |
| 7,179,087 B2 | 2/2007 | Kuhn | |
| 7,828,780 B2 | 11/2010 | Chu | |
| 2002/0117849 A1 | 8/2002 | Bailey | |
| 2002/0119415 A1 | 8/2002 | Bailey | |
| 2004/0003710 A1 | 1/2004 | Pinot | |
| 2004/0014000 A1 | 1/2004 | Bernhard | |
| 2006/0024640 A1 | 2/2006 | Pond et al. | |
| 2006/0135914 A1 | 6/2006 | Chu et al. | |
| 2008/0318185 A1 | 12/2008 | Mizunuma et al. | |

* cited by examiner

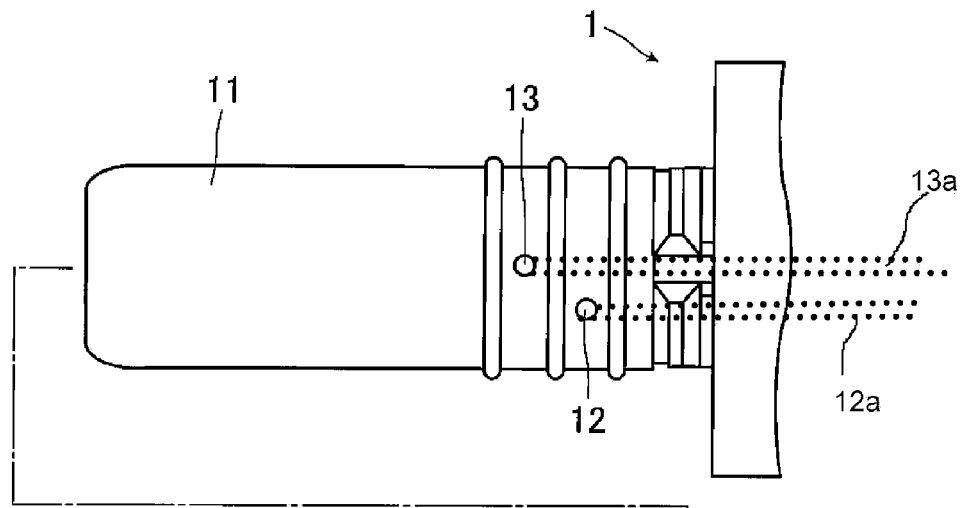
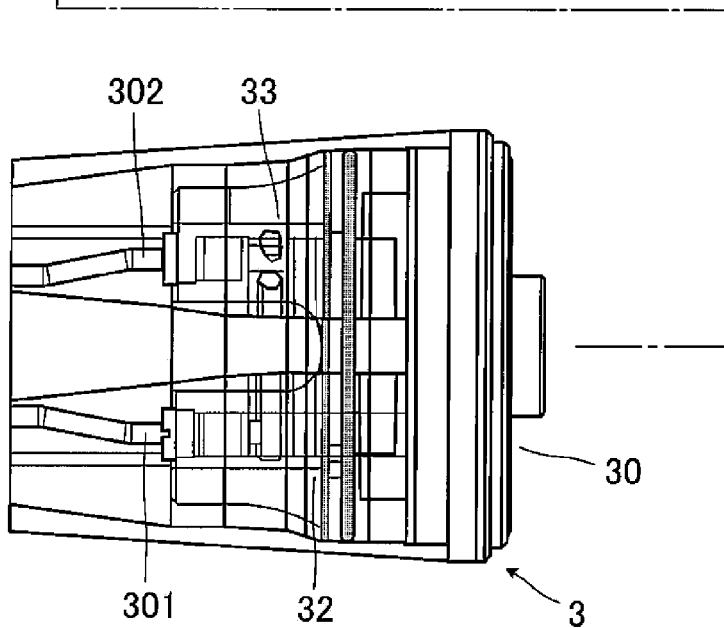
Fig. 7
Prior Art
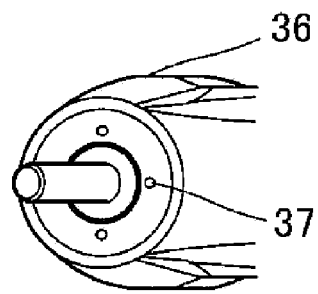
Fig. 8
Prior Art

DENTAL HANDPIECE WITH SWITCHING VALVE FOR FLUID LINES

This is a continuation of application Ser. No. 13/479,455, filed May 24, 2012, abandoned, the disclosure of which is hereby incorporated by reference herein.

FIELD OF ART

The present invention relates to a dental handpiece having fluid lines, in particular, a water spray dental handpiece comprised of a handpiece body and a drive section detachably connected to the handpiece body, wherein, by connecting the drive section to the handpiece body, water and chip air lines in the drive section are connected to the corresponding water and chip air lines in the handpiece body.

BACKGROUND ART

Water spray dental handpieces are conventionally known, with which a dentist may spray water through the tip of the head section of the dental handpiece for cleaning the treatment site or the like. A dental handpiece of this type is known from, for example, JP-3103624-U, and is shown partially in FIGS. 7 and 8 of the attached drawings. The handpiece has a drive section 1 and a handpiece body 3. The drive section 1 has an insert 11 axially projecting in the distal part of the drive section 1, and the handpiece body 3 has an axial bore 30 extending axially and opened in the proximal end face. The drive section 1 is detachably coupled to the handpiece body 3 by inserting the insert 11 into the axial bore 30.

The drive section 1 contains a water line 12a having an outlet aperture 12 opened in the circumferential surface of the insert 11, for transferring water from a water source, and a chip air line 13a having an outlet aperture 13 opened in the circumferential surface of the insert, for transferring chip air from a chip air source.

On the other hand, the handpiece body 3 contains a corresponding water line 301 and a corresponding chip air line 302, both extending to a head section 36 at the distal end of the handpiece body 3. Circumferential grooves 32 and 33 are formed in the inner surface of the handpiece body 3 in the axial bore 30, and communicate with the water and chip air lines 301 and 302, respectively.

When the drive section 1 is connected to the handpiece body 3 by inserting the insert 11 into the axial bore 30, the outlet aperture 12 of the water line 12a in the drive section 1 is brought into communication with the circumferential groove 32 of the handpiece body 3 so that the water lines (12a, 301) in the drive section 1 and the handpiece body 3 are connected. At the same time, the outlet aperture 13 of the chip air line 13a in the drive section 1 is brought into communication with the circumferential groove 33 of the handpiece body 3 so that the chip air lines (13a, 302) in the drive section 1 and the handpiece body 3 are connected.

In this state, water is transferred from the water source through the water lines (12a, 301) to the head section 36, while chip air is transferred from the chip air source through the chip air lines (13a, 302) to the head section 36, where water and chip air is mixed upstream of holes 37, one to four of which are provided in the end face of the head section 36 as shown in FIG. 8 and sprayed through the holes 37.

In a dental handpiece of this type, as discussed above, water and chip air are transferred through the drive section 1 and the handpiece body 3 in separate lines, and mixed in the head section before spraying. It is not possible to switch off the chip air line to stop chip air, while the water line is switched on to allow passage of water only. Thus even if a user of the handpiece wants to use water only depending on the dental procedure, it is not possible to inject only water through the holes 37 in the head section 36 while chip air is stopped.

SUMMARY OF THE INVENTION

It is an object of the present invention to provide a dental handpiece which may selectively inject water and chip air as desired.

According to the present invention, there is provided a dental handpiece with a switching valve for fluid lines, comprising a drive section and a handpiece body detachably connected to a distal end of said drive section, said drive section comprising a first water line for distally transferring water from a water source, a first chip air line for distally transferring chip air from a chip air source, said handpiece body comprising a second water line for distally transferring water, a second chip air line for distally transferring chip air, an axial bore opened in a proximal end face of the handpiece body, a circumferential water channel in communication with said second water line, and a circumferential chip air channel in communication with said second chip air line, both circumferential channels being provided in an inner surface of said handpiece body in the axial bore at an axially offset position from each other, wherein said circumferential water channel and said circumferential chip air channel are positioned such that, when the drive section is connected to the handpiece body, said first water line is in communication with said circumferential water channel for allowing communication between said first and second water lines, and said first chip air line is in communication with said circumferential chip air channel for allowing communication between said first and second chip air lines, characterized in that said handpiece body has a switching valve provided between said circumferential chip air channel and said chip air line for selectively allowing and preventing communication therebetween, wherein opening of said valve switches said communication to an ON-state in which chip air is allowed to pass from said circumferential chip air channel into said chip air line, whereas closing of said valve switches said communication to an OFF-state in which chip air is prevented from passing from said circumferential chip air channel into said chip air line.

The switching valve may further selectively allow and prevent communication between said circumferential water channel and said chip air line, wherein opening of said valve prevents said communication between said circumferential water channel and said chip air line, whereas closing of said valve allows said communication between said circumferential water channel and said chip air line.

The handpiece body may further comprise a valve seat hole provided in communication with said chip air line and axially crossing said circumferential chip air channel, wherein said valve seat hole is sized so as to rotatably receive said switching valve therein around a longitudinal axis. The switching valve may generally be in a form of a hollow cylinder with one end opened and the other end closed, have a first communication port in a circumferential surface in communication with hollow, and be seated in said valve seat hole with said opened end connected to said chip air line. The said first communication port may be located at a circumferential position such that, when said valve is rotated in a predetermined direction to a first position, said first communication port aligns with said circumferential chip air channel to allow communication between said circumferential chip air channel and said chip air line, whereas when said valve is rotated in a reverse direction to a second position, said first communication port is positioned out of alignment with said circumferential chip air channel to prevent communication between said circumferential chip air channel and said chip air line.

The switching valve may further comprise a second communication port in a circumferential surface in communication with hollow, said second communication port being offset circumferentially from said first communication port for a predetermined angle. The second communication port may be located at a circumferential position such that, when said valve is rotated in said predetermined direction to said first position, said second communication port is positioned out of alignment with said circumferential water channel to prevent communication between said circumferential water channel and said chip air line, whereas when said valve is rotated in said reverse direction to said second position, said second communication port aligns with said circumferential water channel to allow communication between said circumferential water channel and said chip air line.

The handpiece body may further comprise a stopper having an end projecting into said valve seat hole through a circumferential wall defining said valve seat hole. The switching valve may further comprise a guide groove provided in the circumferential surface and extends circumferentially for a predetermined angle. The stopper engages said guide groove at said end for relative rotation, and positions said switching valve to said first position when said stopper abuts one end of said guide groove, and to said second position when said stopper abuts the of her end of said guide groove.

BRIEF DESCRIPTION OF THE DRAWINGS

FIG. 7 is a partially fragmented partial longitudinal sectional view of a conventional dental handpiece.

FIG. 8 is a perspective view of a head of the dental handpiece of FIG. 7.

PREFERRED EMBODIMENTS OF THE INVENTION

Figure 1:
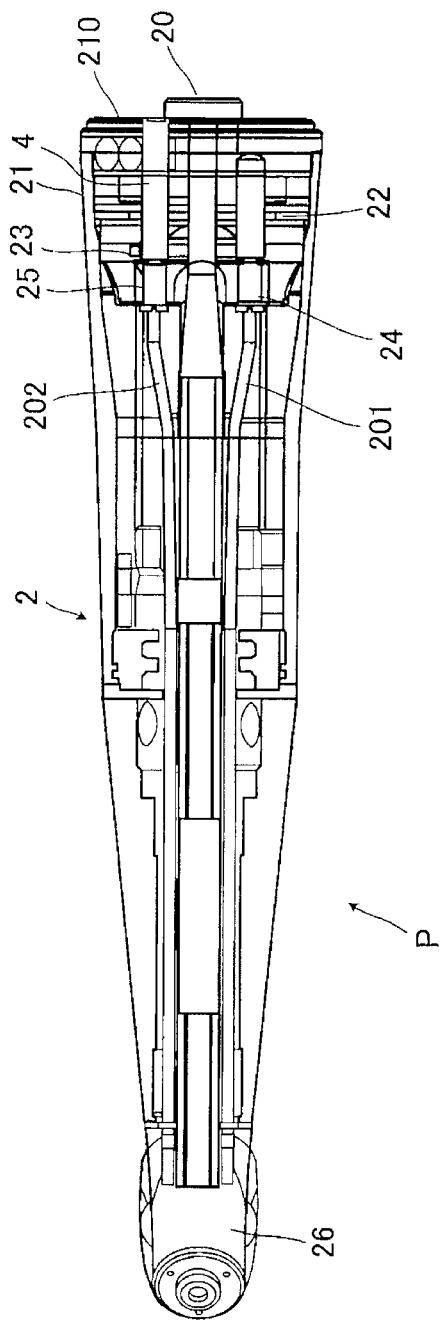
FIG. 1 is a longitudinal sectional view of a handpiece body of a dental handpiece according to one embodiment of the present invention.
Figure 2:
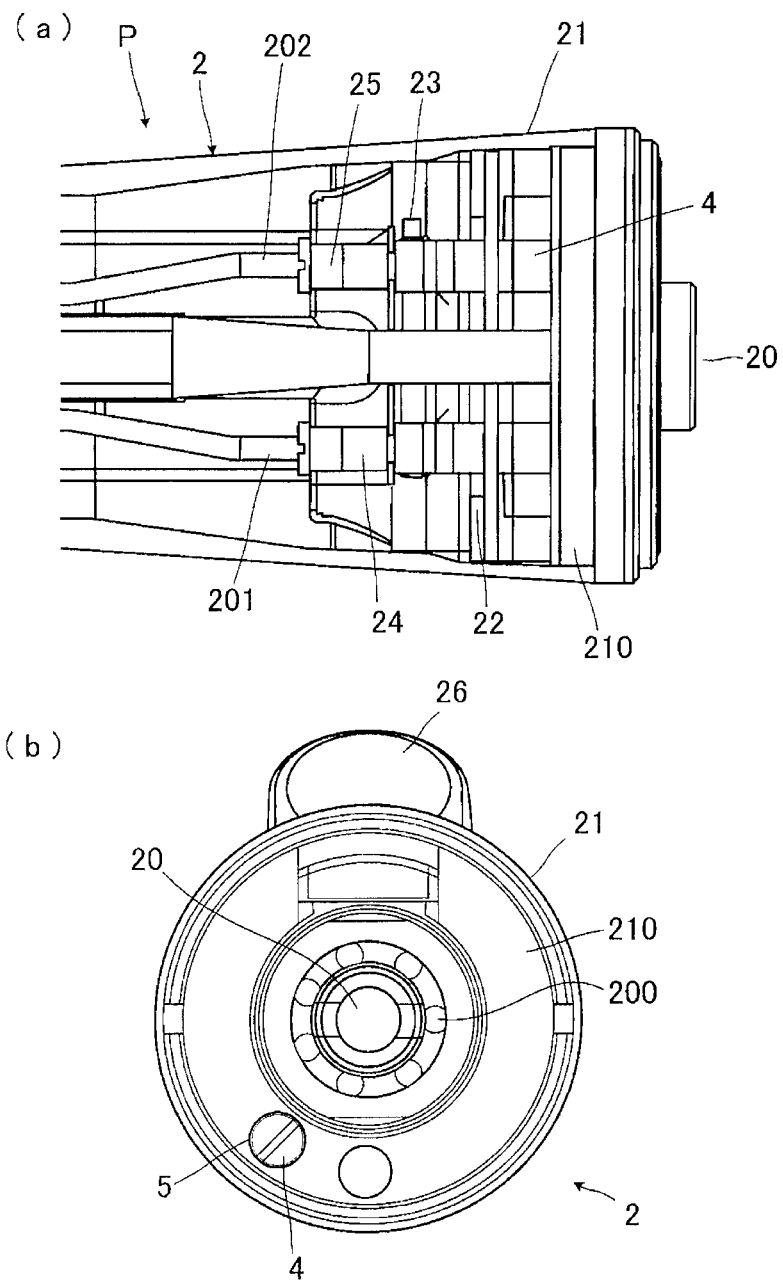
FIG. 2(a) is an enlarged view of the proximal part of the handpiece body of FIG. 1.
FIG. 2(b) is a proximal end view of the handpiece body of FIG. 1.

The present invention will now be explained in detail with reference to the attached drawings. Incidentally, in the embodiment of the dental handpiece shown in FIGS. 1 to 6, the drive section may be a conventional one and thus is not shown in the drawings. When the drive section is referred to in the following detailed description of the invention, reference is made to FIG. 7 showing a drive section of a conventional dental handpiece.

Referring to FIGS. 1 and 2(a), a dental handpiece P according to the present invention has a drive section 1 (FIG. 7) and a handpiece body 2. The drive section 1 has an insert 11 axially projecting in the distal part of the drive section 1, and the handpiece body 2 has an axial bore 20 extending axially and opened in the proximal end face. The drive section 1 is detachably coupled to the handpiece body 2 by inserting the insert 11 into the axial bore 20.

The drive section 1 contains a water line 12a extending therein for transferring water from a water source, and having an outlet aperture 12 opened in the circumferential surface of the insert 11 at a location closer to the proximal end of the insert 11. The drive section 1 also contains a chip air line 13a for transferring chip air from a chip air source, and having an outlet aperture 13 opened in the circumferential surface of the insert 11 at a location closer to the distal end of the insert 11 compared to the aperture 12. The outlet aperture 13 is offset from the outlet aperture 12 circumferentially for a predetermined angle.

Figure 3:
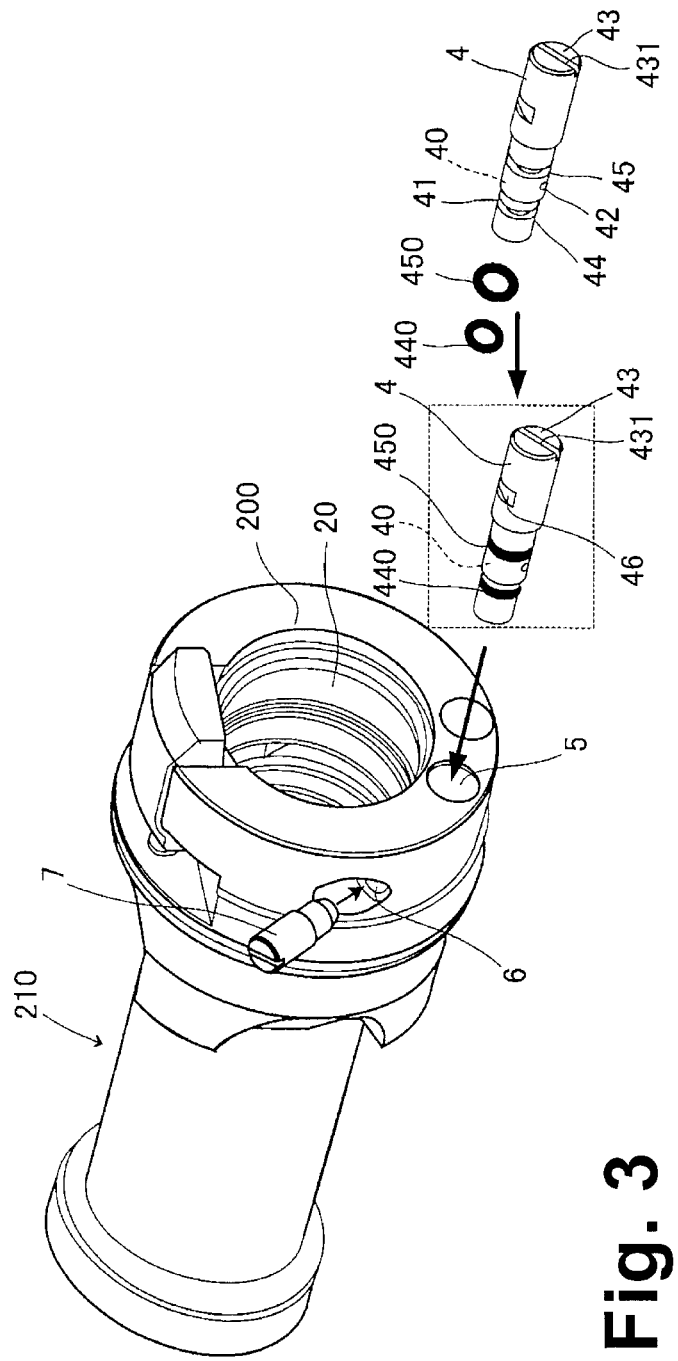
FIG. 3 is an exploded perspective view showing a tubular connector in the handpiece body, having a valve seat hole and a stopper hole, together with a switching valve and a stopper to be seated in the respective holes.

On the other hand, the handpiece body 2 contains a corresponding water line 201 for transferring water, and a corresponding chip air line 202 for transferring chip air, both extending axially to a head section 26 at the distal end of the handpiece body 3. Referring to FIGS. 1 and 3, the handpiece body 2 has a tubular connector 210 fit in the proximal end of a housing 21 and having the axial bore 20 opened in the proximal end face of the handpiece body 2 for receiving the insert 11 therein as mentioned above. The proximal portion of the connector 210 has a thickened wall, and an opening 200 of the axial bore 20 is defined in the proximal end face of the connector 210.

A circumferential channel 22 is formed in the inner surface of the thickened wall of the connector 210 in the axial bore 20, and communicates with the water line 201 via a connection port 24 of the water line 201. The axial position of the circumferential channel 22 is determined so as to be aligned with the outlet aperture 12 of the drive section 1 when the drive section 1 is coupled to the handpiece body 2.

Another circumferential channel 23 is formed in the inner surface of the thickened wall of the connector 210 distal to the circumferential channel 22, and communicates with the chip air line 202 via a connection port 25 of the chip air line 202. The axial position of the circumferential channel 23 is determined so as to be aligned with the outlet aperture 13 of the drive section 1 when the drive section 1 is coupled to the handpiece body 2.

When the drive section 1 is coupled to the handpiece body 2 by inserting the insert 11 into the axial bore 20, the outlet aperture 12 of the water line 12a in the drive section 1 is brought into communication with the circumferential channel 22 of the handpiece body 2 so that the water lines (12a, 301) in the drive section 1 and the handpiece body 2 are connected. At the same time, the outlet aperture 13 of the chip air line 13a in the drive section 1 is brought into communication with the circumferential channel 23 of the handpiece body 2 so that the chip air lines (13a, 302) in the drive section 1 and the handpiece body 2 are connected. In this state, water is transferred through the connected water lines (12a, 301), and chip air is transferred through the connected chip air lines (13a, 302), and mixed in the head section 26 before injection.

Referring to FIGS. 2(a) and 2(b), a switching valve 4 is provided for switching communication between the circumferential channel 23 and the chip air line 202. The switching valve 4 switches the communication between the ON-state wherein chip air is allowed to pass from the circumferential channel 23 into the chip air line 202, and the OFF-state wherein chip air is prevented from passing from the circumferential channel 23 into the chip air line 202.

Referring to FIG. 3, the switching valve 4 is generally in the form of a hollow cylinder having hollow 40 opened to the distal end of the valve 4 and closed to the proximal end. A communication port 41 for chip air is pierced in the circumferential surface of the valve 4 in communication with the hollow 40. The axial position of the port 41 is determined so as to be aligned with the circumferential channel 23 of the connector 210 when the valve is seated in the connector 210 as will be discussed later. A communication port 42 for water, which is optional according to the present invention but is provided in this embodiment, is pierced in the circumferential surface of the valve 4 proximal to the port 41 to communicate with the hollow 40. The port 42 is offset from the port 41 circumferentially for a predetermined angle, e.g., 180°. The axial position of the port 42 is determined so as to be aligned with the circumferential channel 22 of the connector 210 when the valve is seated in the connector 210 as will be discussed later. On the proximal and distal side of the port 42 for water, circumferential grooves 44 and 45 are provided in the circumferential surface of the valve 4, in which O-rings 440 and 450 are fitted, respectively, to seal around the port 42 for water.

The end of the valve 4 opposite to the opening of the hollow 40 forms an operation surface 43 having a slot 431 in which a tool, such as a flat-blade screwdriver, may engage.

A guide groove 46 having a U-shaped cross section, is provided in the circumferential surface of the valve 4 proximal to the port 42, and extends circumferentially for a predetermined angle, e.g., 180°.

A valve seat hole 5 for receiving the switching valve 4 therein is provided axially in the thickened wall of the connector 210, and opened on the proximal end face of the connector 210 next to the opening 200. The valve seat hole 5 is sized such that the valve 4 rotatably fits in the hole 5, and extends in the thickened wall axially crossing the circumferential channels 22 and 23 to the connection port 25 of the chip air line 202 for communicate with the chip air line 202. In this way, the valve seat hole 5 is facing to and positioned coaxially with the connection port 25.

The switching valve 4 is fit and seated in the valve seat hole 5 rotatably around its longitudinal axis, and sealed in the hole 5 with the O-rings 440 and 450.

Figure 4:
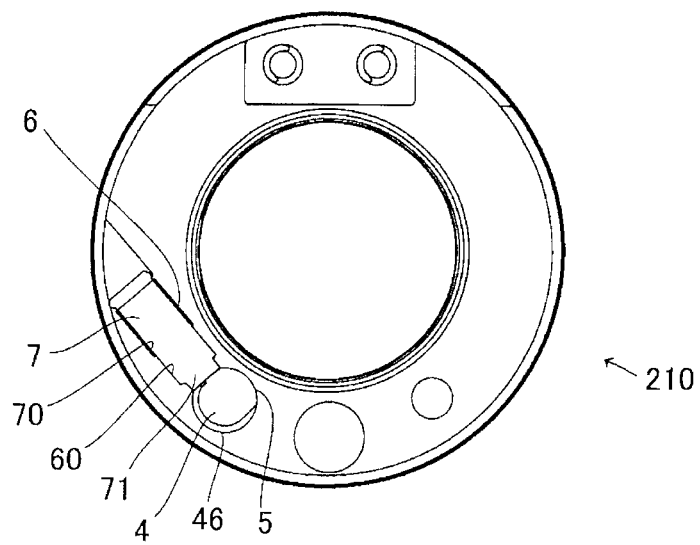
FIG. 4 is a cross sectional view taken near the proximal end of the tubular connector of FIG. 3, with the switching valve and the stopper seated in the valve seat hole and the stopper hole, respectively.

Referring to FIG. 4, a stopper seat hole 6 for receiving a stopper 7 as will be discussed later, is provided in the thickened wall of the connector 210, and opened in the circumferential surface of the connector 210 at one end and in the valve seat hole 5 at the other end. The stopper seat hole 6 extends at an angle to the axially extending valve seat hole 5 and communicates with the hole 5 through its circumferential wall. The stopper seat hole 6 has internal threads 60.

The stopper 7 is generally rod-shaped, and has a thinned distal end portion 71 and external threads 70. The size of the stopper 7 is such that it is screwed into the stopper seat hole 6 with the external threads 70 meshing the internal threads 60, and fixed therein with the thinned distal end portion 71 slightly extending into the valve seat hole 5.

Here, when the switching valve 4 is seated in the valve seat hole 5, the thinned distal end portion 71 of the stopper 7 fixed in the stopper seat hole 6 engages in the circumferential guide groove 46 of the valve 4 for relative rotation. By means of this engagement between the stopper 7 and the valve 4, the valve 4 is prevented from falling out of the valve seat hole 5 and retained securely therein.

In the engaged state, the stopper 7 is relatively guided in the guide groove 46. When the valve 4 is rotated on its longitudinal axis in a predetermined direction until one end of the groove 46 abuts the thinned portion 71 of the stopper 7, the communication port 41 of the valve 4 is aligned with the circumferential channel 23 of the connector 210 for allowing communication between the channel 23 and the chip air line 202 through the port 41. At the same time, the communication port 42 is positioned out of alignment with the circumferential channel 22 of the connector 210 for preventing communication between the channel 22 and the chip air line 202 through the port 42. This is referred to as an opening operation, and shown in FIG. 5. In reverse, when the valve 4 is rotated in the reverse direction until the other end of the groove 46 abuts the thinned portion 71 of the stopper 7, the communication port 42 of the valve 4 is aligned with the circumferential channel 22 of the connector 210 for allowing communication between the channel 22 and the chip air line 202 through the port 42. At the same time, the communication port 41 is positioned out of alignment with the circumferential channel 23 of the connector 210 for preventing communication between the channel 23 and the chip air line 202 through the port 41. This is referred to as a closing operation, and shown in FIG. 6.

The switching valve 4 may be rotated by engaging, for example, a screwdriver in the slot 431 in the operation surface 43 and rotating the screwdriver as in the present embodiment. Preferably, this rotation of the switching valve 4 may be effected with a linking mechanism for realizing the opening and closing operations from external to the handpiece body 2.

In this way, in a dental handpiece having separate water lines and chip air lines in the handpiece body 2 and the drive section 1, by providing a switching valve 4 between the circumferential channel 23 for chip air and the chip air line 202, communication between the channel 23 and the line 202 for chip air may be selectively allowed and prevented easily by a simple rotating operation of the valve 4. Through the opening operation of the valve 4, the circumferential channel 23 in communication with the outlet aperture 13 of the chip air line in the drive section is brought into communication with the chip air line 202 in the handpiece body 3 for allowing passage of chip air into the chip air line 202 in the ON-state. Through the closing operation of the valve 4, the circumferential channel 23 in communication with the outlet aperture 13 is brought out of communication with the chip air line 202 for preventing passage of chip air into the chip air line 202 in the OFF-state.

Figure 5:
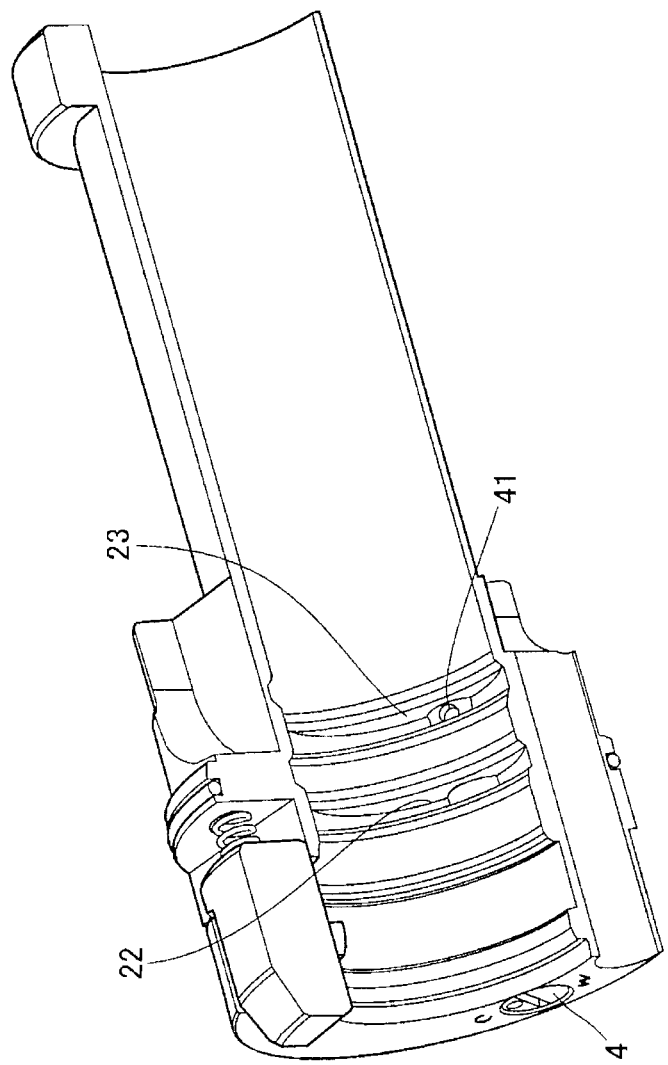
FIG. 5 is a longitudinal sectional view of the tubular connector with the switching valve of FIG. 3, wherein the chip air line is in the ON state.
Figure 6:
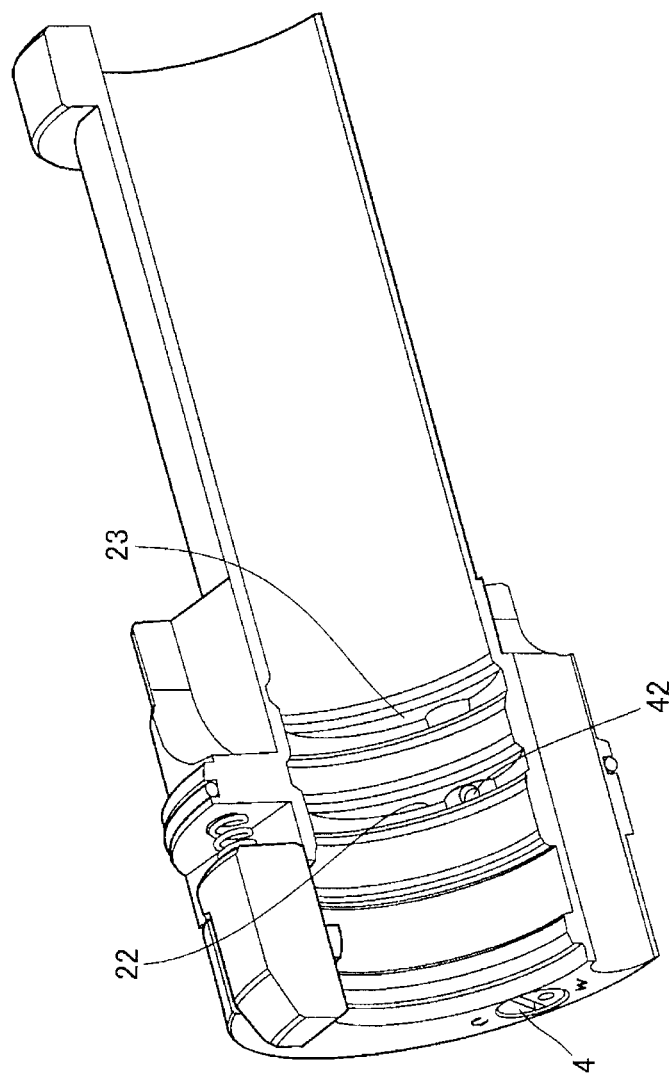
FIG. 6 is a longitudinal sectional view similar to FIG. 5, but with the chip air line in the OFF state.

Further, in the ON-state as shown in FIG. 5, the circumferential channel 22 in communication with the outlet aperture 12 of the water line 12a in the drive section is brought out of communication with the chip air line 202 for preventing passage of water into the chip air line 202. In the OFF-state as shown in FIG. 6, the circumferential channel 22 in communication with the outlet aperture 12 is brought into communication with the chip air line 202 for allowing passage of water into the chip air line 202. Thus water from the drive section 1 is passed into both the water line 201 and the chip air line 202, so that an additional amount of water may be injected through the head section 26.

With the switching valve 4 of the present invention, when both water and chip air are to be used, e.g. for spraying a mixture of water and chip air, the chip air line 202 is switched to the ON-state through the opening operation of the valve 4. In this state, water is passed through the water line 201 while chip air is passed through the chip air line 202. When only water is to be used and chip air is stopped, the chip air line 202 is switched to the OFF-state through the closing operation of the valve 4. In this state, water is passed through the water line 201 and optionally through the chip air line 202, while chip air is stopped. Thus selective water injection may be achieved depending on the dental procedure.

Since the switching valve 4 of the present invention has the guide groove 46, in which the stopper 7 is engaged and guided, the opening and closing operations of the valve 4 may be performed easily and securely. Further, the communication ports 41 and 42 in the valve 4 are securely positioned selectively in alignment with the circumferential channels 23 and 22, respectively.

In the embodiment described above, the switching valve 4 has the communication port 42 for water, but according to the present invention, this communication port 42 may be dispensed with, and only the communication port 41 for chip air is provided in the switching valve. In this case, when the chip air line 202 is switched to the OFF-state through the closing operation of the valve 4, water is passed only through the water line 201 while chip air is stopped. When the chip air line 202 is switched to the ON-state through the opening operation of the valve 4, water and chip air are passed in the same way as in the first embodiment.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece with a switching valve for fluid lines, comprising a drive section and a handpiece body detachably connected to a distal end of said drive section, said drive section comprising a first water line for distally transferring water from a water source, a first chip air line for distally transferring chip air from a chip air source, said handpiece body comprising a second water line for distally transferring water, a second chip air line for distally transferring chip air, an axial bore opened in a proximal end face of the handpiece body, a circumferential water channel in communication with said second water line, and a circumferential chip air channel in communication with said second chip air line, both circumferential channels being provided in an inner surface of said handpiece body in the axial bore at an axially offset position from each other, wherein said circumferential water channel and said circumferential chip air channel are positioned such that, when the drive section is connected to the handpiece body, said first water line is in communication with said circumferential water channel for allowing communication between said first and second water lines, and said first chip air line is in communication with said circumferential chip air channel for allowing communication between said first and second chip air lines, characterized in that said handpiece body has a switching valve provided between said circumferential chip air channel and said second chip air line for selectively allowing and preventing communication therebetween, wherein opening of said valve switches said communication to an ON-state in which chip air is allowed to pass from said circumferential chip air channel into said second chip air line, whereas closing of said valve switches said communication to an OFF-state in which chip air is prevented from passing from said circumferential chip air channel into said second chip air line, wherein said switching valve further selectively allows and prevents communication between said circumferential water channel and said second chip air line, wherein said opening of said valve prevents said communication between said circumferential water channel and said second chip air line, whereas said closing of said valve allows said communication between said circumferential water channel and said second chip air line.

2. The dental handpiece according to claim 1, wherein said handpiece body further comprises a valve seat hole provided in communication with said second chip air line and axially crossing said circumferential chip air channel, wherein said valve seat hole is sized so as to rotatably receive said switching valve therein around a longitudinal axis, wherein said switching valve is generally in a form of a hollow cylinder with one end opened and the other end closed, has a first communication port in a circumferential surface in communication with the hollow, and is seated in said valve seat hole with said opened end connected to said second chip air line, wherein said first communication port is located at a circumferential position such that, when said valve is rotated in a predetermined direction to a first position, said first communication port aligns with said circumferential chip air channel to allow communication between said circumferential chip air channel and said second chip air line, whereas when said valve is rotated in a reverse direction to a second position, said first communication port is positioned out of alignment with said circumferential chip air channel to prevent communication between said circumferential chip air channel and said second chip air line.

3. The dental handpiece according to claim 2, wherein said switching valve further comprises a second communication port in a circumferential surface in communication with the hollow, said second communication port being offset circumferentially from said first communication port for a predetermined angle, wherein said second communication port is located at a circumferential position such that, when said valve is rotated in said predetermined direction to said first position, said second communication port is positioned out of alignment with said circumferential water channel to prevent communication between said circumferential water channel and said second chip air line, whereas when said valve is rotated in said reverse direction to said second position, said second communication port aligns with said circumferential water channel to allow communication between said circumferential water channel and said second chip air line.

4. The dental handpiece according to claim 2, wherein said handpiece body further comprises a stopper having an end projecting into said valve seat hole through a circumferential wall defining said valve seat hole, wherein said switching valve further comprises a guide groove provided in the circumferential surface and extends circumferentially for a predetermined angle, wherein said stopper engages said guide groove at said end for relative rotation, and positions said switching valve to said first position when said stopper abuts one end of said guide groove, and to said second position when said stopper abuts the other end of said guide groove.

5. The dental handpiece according to claim 3, wherein said handpiece body further comprises a stopper having an end projecting into said valve seat hole through a circumferential wall defining said valve seat hole,
   wherein said switching valve further comprises a guide groove provided in the circumferential surface and extends circumferentially for a predetermined angle,
   wherein said stopper engages said guide groove at said end for relative rotation, and positions said switching valve to said first position when said stopper abuts one end of said guide groove, and to said second position when said stopper abuts the other end of said guide groove.

* * * * *